United States Patent [19]

Sommer et al.

[11] 4,299,730

[45] Nov. 10, 1981

[54] PROCESS FOR THE PRODUCTION OF A CATALYST FOR THE HYDRATION OF OLEFINS INTO ALCOHOLS

[75] Inventors: August Sommer, Herne; Rainer Brücker, Castrop-Rauxel, both of Fed. Rep. of Germany

[73] Assignee: Chemische Werke Huls Aktiengesellschaft, Herne, Fed. Rep. of Germany

[21] Appl. No.: 124,758

[22] Filed: Feb. 26, 1980

[30] Foreign Application Priority Data

Mar. 5, 1979 [DE] Fed. Rep. of Germany ....... 2908491

[51] Int. Cl.$^3$ .................... B01J 27/14; B01J 29/06
[52] U.S. Cl. ............................. 252/435; 252/455 R
[58] Field of Search ..................................... 252/435

[56] References Cited

U.S. PATENT DOCUMENTS

| | | | |
|---|---|---|---|
| 2,377,092 | 5/1945 | McGrew | 252/435 X |
| 2,748,090 | 5/1956 | Watkins | 252/435 X |
| 3,560,586 | 2/1971 | Kronig et al. | 252/435 X |
| 3,704,329 | 11/1972 | Rindtorff et al. | 252/435 X |
| 4,142,994 | 3/1979 | Alofandi | 252/455 R X |

FOREIGN PATENT DOCUMENTS

| | | |
|---|---|---|
| 1156772 | 11/1963 | Fed. Rep. of Germany . |
| 2625705 | 12/1976 | Fed. Rep. of Germany . |
| 2719055 | 11/1977 | Fed. Rep. of Germany . |
| 2658946 | 7/1978 | Fed. Rep. of Germany . |
| 463272 | 3/1937 | United Kingdom ............... 252/435 |

*Primary Examiner*—Delbert E. Gantz
*Assistant Examiner*—William G. Wright
*Attorney, Agent, or Firm*—Oblon, Fisher, Spivak, McClelland & Maier

[57] ABSTRACT

A process for producing a clay-containing catalyst for the hydration of olefins having 2-3 carbon atoms into alcohols, which comprises: (A) acid-treating a montmorillonite-containing clay which is contaminated by not more than 3% of quartz, feldspar or mica, and which may contain up to 0.5% of $K_2O$, until the clay has an $Al_2O_3$ content of 13–18% by weight, thereby obtaining a surface area of 200–400 m$^2$/g; (B) molding the clay at a total water content of 20–35%; (C) calcining at 500°–800° C.; (D) acid-treating the molded and calcined clay to an $Al_2O_3$ content of 1–5% by weight, thereby obtaining a surface area of 150–250 m$^2$/g; and (E) impregnating said material with phosphoric acid.

14 Claims, No Drawings

4,299,730

PROCESS FOR THE PRODUCTION OF A CATALYST FOR THE HYDRATION OF OLEFINS INTO ALCOHOLS

BACKGROUND OF THE INVENTION

1. Field of the Invention

The present invention relates to a process for preparing a catalyst for the hydration of olefins into alcohols.

2. Description of the Prior Art

It is known that olefins can be transformed into alcohols in the gas phase under increased pressure with water vapor. Such processes have achieved a special technical importance in the production of ethyl alcohol from ethylene, and isopropyl alcohol from propylene. The syntheses of these alcohols is carried out in the presence of catalysts and, generally phosphoric acid applied to carrier serves as catalyst.

Carrier materials are known either on the basis of pure silicic acid (for example, siliceous earth or silica gel) or on the basis of silicic acid with a more or less high content of pure clay, such as, for example, calcined diatomaceous earth whose structure is held together by clay or clay-like materials.

In the case of carriers on the basis of pure silicic acid, the stability creates a problem over longer periods of time. Materials containing pure clay actually have a better mechanical stability but, with too high a content of pure clay, they have the disadvantage that the aluminum oxide is separated during the reaction, by the action of the phosphoric acid, leading to interfering deposits in the subsequently connected units.

It has also become possible to develop carriers for phosphoric acid with a high hydration activity and sufficient mechanical stability on the basis of coarse-pored silica gels, see for example, German Laid Open Patent Publications 26 25 705 and 27 19 055. However, there remains the disadvantage of these carriers on the basis of amorphous silicic acid that, with a longer exposure against the conditions of the hydration reaction, the amorphous silicic acid partially crystallizes to cristobalite and quartz, which is connected with a high reduction of the specific surface and thus of the catalytic activity in an irreversible manner, as well as with a decrease in the mechanical stability.

A process for the production of a pure clay-containing carrier has been described in German Patent No. 11 56 772 for the phosphoric acid used in the olefin hydration as catalyst in which molded contact bodies of mineral clay silicates, particularly commercially available bentonite-containing contact bodies for hydrogenations and dehydrogenations, are treated in such a way with mineral acid that the aluminum oxide content is preferably lowered to between 1 and 5% by weight. This material has the necessary mechanical stability as well as a sufficiently low remaining aluminum oxide content in order to avoid a deposit in subsequently connected units by components separated with phosphoric acid. In the course of the experience of many years with the use of commercially available bentonite-containing contact bodies for hydrogenations and dehydrogenations, it was now observed that, with the production of the commercially available contact bodies for the purpose of hydrogenation and dehydrogenation it is not necessary to the same degree to make a preliminary selection concerning the raw material as for the production of the carrier material for phosphoric acid. Thus, the hydration catalysts produced by acid treatment and impregnation with phosphoric acid from commercially available bentonite-containing contact bodies show greatly varying activities which leads to strong fluctuations of the plant capacity with existing reactor volume in continuously operating synthesis plants.

Since it has been determined in the meantime that the life of the catalyst is considerably prolonged by a continuous injection of the discharged amounts of phosphoric acid (German Laid Open Publication 26 58 946) and thus corresponding claims are also to be made to the life of the carrier, the use of such carriers is excluded in the case of which, under reaction conditions, a reduction occurs in the catalytic activity, for example, crystallizations take place in an irreversible manner and/or the mechanical stability is reduced in the course of time.

SUMMARY OF THE INVENTION

It has now been surprisingly determined that carriers for hydration catalysts with a constant high catalytic activity can be obtained from clay minerals produced with certain clays when precautions are taken by the careful selection of the raw material that the material consists, to a high degree, of montmorillonite and does not contain more than 5 g potassium (computed as $K_2O$) per kg of clay.

It was, furthermore, determined that there is a dependence of the catalytic activity (expressed in the highest possible alcohol production per volume catalyst preparation and time) on the specific surface of the carrier after the impregnation with phosphoric acid and adjusting of the phosphoric acid concentration present under operating conditions after the second acid treatment. This dependence shows up in the fact that the best catalytic values are obtained when the specific surface is at about 200 $m^2/g$ after the second acid treatment but before the impregnation.

The object of the invention is, therefore, a process for the production of a catalyst of clay minerals for the hydration of olefins with 2-3 C-atoms into the respective alcohols, of phosphoric acid and carrier material, wherein an essentially montmorillonite-containing clay which is contaminated by not more than 3% accompanying materials, such as quartz, feldspar and mica, and which can contain up to 0.5% $K_2O$ is initially treated in a first stage with acid until it has an $Al_2O_3$-content of 13–18% by weight and, if necessary, the $Al_2O_3$-content is adjusted to 16–18% by weight of adding precipitated pure clay whereby a surface of 200–400 $m^2/g$, preferably 240–300 $m^2/g$, is obtained, then molded by squeezing with a total water content of 20–30%, calcined at 500°–800° C. and, subsequently, the molded carrier material is treated in a second stage with acid to an $Al_2O_3$-content of 1–5%, preferably 1–3% by weight, whereby a surface of 150–250 $m^2/g$, preferably 180–220 $m^2/g$, is obtained and the carrier obtained in this way is impregnated with phosphoric acid in a known manner.

The object of the invention is, furthermore, a catalyst for the hydration of olefins as described above.

DESCRIPTION OF THE PREFERRED EMBODIMENTS

When investigating the specific surface of the carrier on montmorillonite basis treated only once by acid, it can be determined that it is between 200 and 400 $m^2/g$, preferably 240–300 $m^2/g$.

The carrier treated twice with acid but not impregnated with phosphoric acid shows a specific surface of 150–250 m²/g, preferably 180–220 m²/g.

Additionally, a certain dependence was determined of the catalytic activity on the surface of the used material so that a higher activity could be achieved with smaller than customary (5 mm) sphere or cylinder diameters, i.e., 2 to 5 mm.

The particularity of the clay type montmorillonite with the summation formula $Al_2(Si_4O_{10})(OH)_2$ consists of the fact that a layer of $Al_2O_3$-octahedra is always enclosed by 2 layers of $SiO_2$-tetrahedra whereby residual charges are saturated by protons. The aluminum can be separated to a large extent by the thermal acid treatment whereby, initially, an enlargement of the surface occurs as long as only negative charges left by the aluminum on the remaining $SiO_2$-tetrahedra are saturated by protons but the montmorillonite layer structure is maintained.

Only when with the further separation of aluminum the montmorillonite structure is destroyed, the surface is again reduced. However, this area must be reached with the carriers for phosphoric acid-containing hydration catalysts in order to avoid the separation of aluminum salts of the phosphoric acid in the subsequently connected units which would form in case of too high a residual aluminum content with phosphoric acid.

In the case of the minerals mica and feldspar which belong to the group of the alumino-silicates, there are not, as in the case of montmorillonite, exclusively cationic layers of aluminum but aluminum is entirely (feldspar) or partially (mica) incorporated in the $SiO_2$-tetrahedron lattice whereby excessive negative charges are predominantly saturated by potassium cations. With the acid treatment of mica $K\,Al_2(Al\,Si_3\,O_{10})(OH)_2$ and feldspar $K(Al\,Si_3O_8)$, the cations potassium (in the case of mica, also the Al outside the bracket) but not the aluminum incorporated in the silicate structure are replaced by protons. Thus, the loosening of the crystal structure with the acid treatment, in comparison with the montmorillonite, is eliminated and, therefore, also the enlargement of the surface.

Other minerals of the montmorillonite group which do not contain potassium and also have the same crystal lattice as montmorillonite with only a few defective points caused by impurity ions, are included in these considerations since they behave analogously with the pure montmorillonite during the two-stage acid treatment. These are saponified with magnesium instead of aluminum in the octahedron, hectorite with, additionally, lithium to the magnesium, nontronite with iron and sauconite with zinc at this point as well as beidellite with aluminum in the tetrahedron lattice of the silicium.

Therefore, an optimum surface of the molded contact bodies is to be expected with the use of such raw clays which have a maximum montmorillonite content because only this mineral contributes to the enlargement of the surface after treatment with acid. The two minerals mica and feldspar have in common their potassium content without contribution to the enlargement of the surface which is extracted by the treatment with acid. Therefore, a statement can be made by means of the potassium determination of the extract with a 15–20% hydrochloric acid at 80°–90° C. as to whether a certain raw material is suitable for the production of carrier material for the hydration catalyst.

Purely analytically, the dry substance in mica contains 12% $K_2O$, in feldspar 17% $K_2O$. When a $K_2O$ content in the raw clay (with reference to the dry substance) of below 0.5% is obtained from the potassium quantity extractable through the treatment with hydrochloric acid, it can be assumed that a specific surface of 200–400 m²/g is obtained and that the molded contact body has a sufficiently large specific surface (150–250 m²/g) after the second treatment with acid, in order to have optimum properties as a carrier for hydration catalysts.

Commercially available highly active bleaching earth has been produced from corresponding clay by means of the treatment with acid as in the first stage where the aluminum content was reduced to 13–18% by weight. However, it can be used exactly as a clay having the mentioned properties after the first acid treatment stage.

EXAMPLE 1

A ground natural raw clay which was selected on the basis of a laboratory examination showing that not more than 5 g $K_2O$ per kg of used dry substance are extracted with a one-hour treatment with a 20% hydrochloric acid at 82° C. was heated for one hour with a 20% hydrochloric acid to 82° C. whereby the amount of acid was such that 8.4 mol HCl were used for 1 kg clay, washed acid-free and dried. In this way, a substance with a residual aluminumoxide content of 16% and a specific surface of 310 m²/g was obtained.

After pre-wetting with 25% water with reference to the total amount (this means adding 33% of the dry substance as water), the substance was pressed into a cylindrical mold with a diameter of 4 mm and a height of 4 mm and stabilized by heating it for 3 hours, to 600° C.

The molded contact bodies obtained in this way were, in all, twice treated with a 20% hydrochloric acid for one hour at 100° to 110° C. and washed free from acid with water. After the drying at about 110°–120° C., an aluminum oxide content of 2.9% was determined in the cylinders and the specific surface amounted to 230 m²/g.

These molded bodies were then flooded with a 60% by weight phosphoric acid which was allowed to react for two hours and subsequently they were again subjected to a drying process at about 110°–120° C. The cylinders treated in this manner had a $H_3PO_4$- content of 38% by weight.

With the use of the hydration catalyst produced in this way for the synthesis of ethanol from ethylene and water in the gas phase, a catalyst yield of 105 g ethanol per h and 1 catalyst charge could be obtained in comparison with 80 g ethanol per h and 1 catalyst charge which are obtained when proceeding in accordance with the German Disclosure Publication 11 56 772 under the same reaction conditions.

EXAMPLE 2

A ground natural raw clay which was selected on the basis of a laboratory examination showing that not more than 5 g $K_2O$ per kg of used dry substance are extracted with a one-hour treatment with a 20% hydrochloric acid at 82° C. was heated for one hour with a 20% hydrochloric acid to 82° C. whereby the amount of acid was such that 8.4 mol HCl were used for 1 kg clay, washed acid-free and dried. In this way, a substance with a residual aluminum oxide content of 14% and a specific surface of 270 m²/g was obtained. By adding precipitated pure clay in the amount of 3% of the weight of the dried substance, the Al$_2$O$_3$-content was adjusted to 17%.

After pre-wetting with 30% water with reference to the total amount (this means adding 43% of the dry substance as water), the substance was pressed into spheres with a diameter of 3 mm and stabilized by heating it for 3 hours to 700° C.

The molded contact bodies obtained in this way were, in all, twice treated with a 20% hydrochloric acid for one hour at 100° to 110° C. and washed free from acid with water. After the drying at about 110°–120° C., an aluminum oxide content of 1.8% was determined in the spheres and the specific surface amounted to 180 m$^2$/g. These molded bodies were then flooded with a 60% by weight phosphoric acid which was allowed to react for two hours and subsequently they were again subjected to a drying process at about 110°–120° C. The spheres treated in this manner had a H$_3$PO$_4$-content of 37% by weight.

With the use of the hydration catalyst produced in this way for the synthesis of ethanol from ethylene and water in the gas phase, a catalyst yield of 110 g ethanol per h and 1 catalyst charge could be obtained. In spite of the lower specific surface of the extracted molded bodies, the catalyst activity is somewhat higher than in Example 1 because the surface of the charged bodies has become larger owing to the smaller diameter of the spheres.

EXAMPLE 3

A highly active bleaching earth with a specific surface of 260 m$^2$/g and the following chemical analysis: 72.5% SiO$_2$, 14.0% Al$_2$O$_3$, 4.0% Fe$_2$O$_3$, 1.5% MgO, 0.0% CaO, 7.2% annealing loss, K$_2$O<0.1% was pre-wetted with 30% water with reference to the total amount (this means adding 43% of the dry substance as water) and molded into spheres with a diameter of 4 mm and stabilized by heating for 3 hours to 600° C.

The molded contact bodies obtained in this way were, in all, twice treated with a 20% hydrochloric acid for one hour at 100° to 110° C. and washed free from acid with water. After the drying at about 110°–120° C., an aluminum oxide content of 1.5% was determined in the spheres and the specific surface amounted to 190 m$^2$/g. These molded bodies were then flooded with a 60% by weight phosphoric acid which was allowed to react for two hours and subsequently they were again subjected to a drying process at about 110°–120° C. The spheres treated in this manner had a H$_3$PO$_4$-content of 38% by weight.

With the use of the hydration catalyst produced in this way for the synthesis of ethanol from ethylene and water in the gas phase, a catalyst yield of 110 g ethanol per h and 1 catalyst charge could be obtained.

With the use of this substance for the synthesis of isopropyl alcohol from propylene and water in the gas phase, a catalyst yield of 300 g of isopropyl alcohol could be obtained per h and 1 catalyst charge; with material according to the German Disclosure Publication 11 56 772, 220 g isopropyl alcohol could be obtained per h and 1 catalyst charge under the same reaction conditions.

What is new and intended to be covered by letters patent of the United States is:

1. A process for producing a clay-containing catalyst for the hydration of olefins having 2-3 carbon atoms into alcohols, which comprises:
   (A) acid-treating a montmorillonite-containing clay which is contaminated by not more than 3% of quartz, feldspar or mica, or mixtures thereof, and which may contain up to 0.5% K$_2$O, until said clay has an Al$_2$O$_3$ content of 13–18% by weight, thereby obtaining a surface area of 200–400 m$^2$/g;
   (B) molding said clay at a total water content of 20–35%; then
   (C) calcining said clay at 500°–800° C.;
   (D) acid-treating said molded and calcined clay to an Al$_2$O$_3$ content of 1–5% by weight, thereby obtaining a material with a surface area of 150–250 m$^2$/g; and then
   (E) impregnating said material with phosphoric acid.

2. The process of claim 1, wherein said acid treatment step (A) further comprises adding substantially pure clay to obtain an Al$_2$O$_3$ content of 16–18% by weight.

3. The process of claim 1, wherein said acid treatment step (A) is carried out to obtain a surface area of 240–300 m$^2$/g.

4. The process of claim 1, wherein said acid treatment in step (D) is carried out to an Al$_2$O$_3$ content of 1–3% by weight.

5. The process of claim 1, wherein said acid treatment in step (D) is carried out to obtain a surface area of 180–220 m$^2$/g.

6. The process of claim 1, wherein said starting montmorillonite-containing clay also comprises other minerals having the montmorillonite crystal lattice, but which do not contain potassium.

7. The process of claim 1, wherein said montmorillonite-containing clay is a highly active bleaching earth which contains less than 0.1% K$_2$O, having a weight ratio of (Al$_2$O$_3$+Fe$_2$O$_3$): SiO$_3$ of 1:3.5 to 1:4.5.

8. The process of claim 7, wherein, after treating said highly active bleaching earth with acid according to step (A), said earth is treated with substantially pure clay in order to adjust the surface area of said earth to 16–18%.

9. The process of claim 1, wherein said molding step (B) is carried out to form contact bodies having a diameter of 2–5 mm.

10. The process of claim 9, wherein said diameter is 2–3 mm.

11. The process of claim 9, wherein said contact bodies are spherical.

12. The process of claim 9, wherein said contact bodies are cylindrical.

13. The process of claim 9, wherein said contact bodies are in the form of tablets.

14. A catalyst prepared by the process of claim 1.

* * * * *